US006685657B2

(12) United States Patent
Jones

(10) Patent No.: US 6,685,657 B2
(45) Date of Patent: *Feb. 3, 2004

(54) METHODS FOR SELECTIVELY DISSOLVING AND REMOVING MATERIALS USING ULTRA-HIGH FREQUENCY ULTRASOUND

(76) Inventor: Joie P. Jones, 2094 San Remo Dr., Laguna Beach, CA (US) 92651-2628

( * ) Notice: Subject to any disclaimer, the term of this patent is extended or adjusted under 35 U.S.C. 154(b) by 0 days.

This patent is subject to a terminal disclaimer.

(21) Appl. No.: 09/944,829

(22) Filed: Aug. 31, 2001

(65) Prior Publication Data

US 2002/0000763 A1 Jan. 3, 2002

Related U.S. Application Data

(62) Division of application No. 09/196,847, filed on Nov. 20, 1998, now abandoned.

(51) Int. Cl.$^7$ .................................................. A61H 1/02
(52) U.S. Cl. ............................. 601/2; 606/169; 604/22
(58) Field of Search ................................ 600/437–472; 601/1–4; 606/169; 604/22

(56) References Cited

U.S. PATENT DOCUMENTS

| 2,803,129 A | 8/1957 | Bradfield |
| 3,631,383 A | 12/1971 | Zilinskas |
| 3,827,115 A | 8/1974 | Bom |
| 3,925,692 A | 12/1975 | Leschek et al. |
| 3,941,122 A | 3/1976 | Jones |
| 4,040,414 A | 8/1977 | Suroff |
| 4,166,967 A | 9/1979 | Benes et al. |
| 4,441,486 A | 4/1984 | Pounds |
| 4,578,611 A | 3/1986 | Sadler |
| 4,750,488 A | 6/1988 | Wuchinich et al. |
| 4,808,153 A | 2/1989 | Parisi |
| 4,820,260 A | 4/1989 | Hayden |
| 4,827,911 A | 5/1989 | Broadwin et al. |
| 4,870,953 A | 10/1989 | DonMichael et al. |
| 4,906,238 A | 3/1990 | Greenfeld et al. |

(List continued on next page.)

OTHER PUBLICATIONS

Aslanides, et al., "High Frequency ultrasound imaging in pupillary block glaucoma" British Journal of Ophthalmology 79:972–976 (1995).

Chandraratna, et al., "Characterization of collagen by high–frequency ultrasound: Evidence for different acoustic properties based on collagen fiber morphologic characteristics" American Heart Journal 133 (3):364–368 (1997).

(List continued on next page.)

Primary Examiner—Francis J. Jaworski
Assistant Examiner—William C Jung
(74) Attorney, Agent, or Firm—Michael Blaine Brooks. P.C.; Michael Blaine Brooks; June Learn

(57) ABSTRACT

The present invention provides processes and apparatus for selectively dissolving and removing unwanted solid and semi-solid materials and the like, within a highly localized region utilizing ultra-high energy acoustical waves having a frequency in the range above 50 MHz, for example from about 50 MHz to about 100 GHz. The invention apparatus includes a piezoelectric transducer that is modified to increase the amplitude of acoustical waves of a given frequency without increase in power to the system. The invention and apparatus have important applications in surgical procedures for the treatment of atherosclerotic plaque, prostate disorders, cancers, orthopedic and cosmetic surgery, various types of orthopedic surgery, including atheroscopic surgery, and the like. The present invention is also useful in a wide variety of non-surgical applications, including industrial processes, wherein materials are desired to be selectively removed in a very localized region.

17 Claims, 3 Drawing Sheets

U.S. PATENT DOCUMENTS

| | | |
|---|---|---|
| 4,911,170 A | 3/1990 | Thomas, III et al. |
| 4,936,281 A | 6/1990 | Stasz |
| 5,013,241 A | 5/1991 | von Gutfeld et al. |
| 5,069,664 A | 12/1991 | Guess et al. |
| 5,117,832 A * | 6/1992 | Sanghvi et al. ............. 310/334 |
| 5,125,137 A | 6/1992 | Corl et al. |
| 5,176,141 A | 1/1993 | Bom et al. |
| 5,221,870 A | 6/1993 | Nakahata et al. |
| 5,261,922 A * | 11/1993 | Hood .......................... 606/167 |
| 5,269,291 A | 12/1993 | Carter |
| 5,295,484 A | 3/1994 | Marcus et al. |
| 5,307,816 A | 5/1994 | Hashimoto et al. |
| 5,318,570 A * | 6/1994 | Hood et al. ................... 606/99 |
| 5,324,297 A * | 6/1994 | Hood et al. ................... 606/99 |
| 5,329,682 A | 7/1994 | Thurn et al. |
| 5,332,943 A | 7/1994 | Bhardwag |
| 5,362,309 A * | 11/1994 | Carter .......................... 604/22 |
| 5,431,663 A | 7/1995 | Carter |
| 5,443,069 A | 8/1995 | Schaetzle |
| 5,460,595 A | 10/1995 | Hall et al. |
| 5,474,071 A | 12/1995 | Chapelon et al. |
| 5,474,530 A | 12/1995 | Passafaro et al. |
| 5,524,620 A | 6/1996 | Rosenschein |
| 5,526,815 A | 6/1996 | Granz et al. |
| 5,558,092 A | 9/1996 | Unger et al. |
| 5,601,526 A | 2/1997 | Chapelon et al. |
| 5,606,974 A | 3/1997 | Castellano et al. |
| 5,620,409 A | 4/1997 | Venuto et al. |
| 5,624,382 A | 4/1997 | Oppelt et al. |
| 5,630,837 A | 5/1997 | Crowley |
| 5,666,954 A | 9/1997 | Chapelon et al. |
| 5,676,151 A | 10/1997 | Yock |
| 5,695,460 A | 12/1997 | Siegel et al. |
| 5,695,510 A * | 12/1997 | Hood .......................... 606/169 |
| 5,725,494 A | 3/1998 | Brisken |
| 5,728,062 A | 3/1998 | Brisken |
| 5,733,315 A | 3/1998 | Burdette et al. |
| 5,735,280 A | 4/1998 | Sherman et al. |
| 5,735,811 A | 4/1998 | Brisken |
| 5,740,596 A | 4/1998 | Corl et al. |
| 5,746,756 A | 5/1998 | Bromfield et al. |
| 5,762,066 A * | 6/1998 | Law et al. ................... 600/439 |
| 5,810,009 A | 9/1998 | Mine et al. |
| 5,810,860 A | 9/1998 | Adrian |
| 5,813,998 A | 9/1998 | Dias |
| 5,823,962 A | 10/1998 | Schaetzle et al. |
| 5,827,203 A | 10/1998 | Nita |
| 5,935,142 A * | 8/1999 | Hood .......................... 606/169 |
| 5,935,143 A * | 8/1999 | Hood .......................... 606/169 |
| 5,938,612 A * | 8/1999 | Kline-Schoder et al. .... 310/334 |
| 6,074,349 A * | 6/2000 | Crowley ..................... 600/463 |
| 6,433,464 B2 * | 8/2002 | Jones ......................... 310/328 |

OTHER PUBLICATIONS

Ernst, et al., "Abiltiy of High–Intensity Ultrasound to Ablate Human Atherosclerotic Plaques and Minimize Debris Size" The American Journal of Cardiology 68:242–246 (1991).

Gelet, "Treatment of Prostate Cancer with Transrectal Focused Ultrasound: Early Clinical Experience" Eur Urol 29:174–183 (1996).

Gniadecka, M., "Localization of dermal edema in lipodermato–sclerosis, lyphedema, and cardiac insuffiency" J AM Acad Dermatol 35:37–41:37–41 (1996).

ter Haar, G.T., "Ultrasound Focal Beam Surgery" Ultrasound in Med. & Biol. 21 (9):1089–1100 (1995).

Harland, et al., "High frequency, high resolution B–scan ultrasound in the assessment of skin tumours" British Journal of Dermatology 128:525–532 (1993).

Nielsen, "Small Arteries Can Be Accurately Studied in Vivo Using High Frequency Ultrasound" Ultrasound in Med. & Biol. 19 (9):717–725 (1993).

Siegel, et al., "Percutaneous Ultrasonic Angioplasty: Initial Clinical Experience" The Lancet pp 772–774 (1989).

Siegel, et al., "Use of Therapeutic Ultrasound in Percutaneous Coronary Angioplasty" Circulation 89 (4):1587–1592 (1994).

Tong, et al., "A Three–Dimensional Ultrasound Prostate Imaging System" Ultrasound in Med. & Biol. 22 (6):735–746 (1996).

Watkin, et al., "The urological applications of focused ultrasound surgery" British Journal of Urology 75 Suppl. 1 pp 1–8 (1995).

* cited by examiner

METHODS FOR SELECTIVELY DISSOLVING AND REMOVING MATERIALS USING ULTRA-HIGH FREQUENCY ULTRASOUND

CROSS-REFERENCE TO RELATED APPLICATION

This is a division of application Ser. No. 09/196,847, filed Nov. 20, 1998 now abandoned.

FIELD OF THE INVENTION

The present invention relates to methods for removing materials utilizing ultra-high frequency acoustical waves, especially as related to surgical procedures.

BACKGROUND OF THE INVENTION

It is known in the art to use relatively low ultrasonic frequency energy for a wide variety of purposes ranging from communications to polishing. Of particular interest in the art is removal of soft tissue from inaccessible locations.

U.S. Pat. No. 3,589,363 describes a vibratory assembly for removing material from relatively inaccessible regions. This instrument uses a rapidly vibrating knife tip to break down unwanted material into small particles. As the vibrating tip is applied to the material, the region adjacent to the operative site is flooded with fluid. The unwanted material is dispersed into the fluid which, in turn, is removed by suction. Although the vibrating tip will, as a result of this motion, produce an acoustical wave which propagates into the unwanted material, it is recognized in the art that the cutting motion of the tip, and not just the propagation of radiated acoustical energy, produces the desired action and result. (See, for example, C. D. Kelman, "A Personal Interview Between the Editor and Dr. Charles D. Kelman," *Boyd's Highlights of Ophthalmology*, Volume XIII, No. 1, 1970–71 Series, p. 43.)

This type of technique, often referred to as phakoemulsification, is perhaps the most widely used "ultrasound" technique for removal of cataracts. Since the vibrating tip (or knife) used to cut away the material vibrates at a frequency of 30–40 kHz, it has been termed an "ultrasonic" method even though the device does not rely upon the propagation of an acoustical wave to cut away tissue. Although effective for what it does, the device is essentially a miniaturized electric knife. Some phako-devices operate at sufficient power levels or have sufficient tip excursions to generate cavitation bubbles. Such bubbles, when they implode, generate sufficient energy to break down material and can, in certain situations, create significant bioeffects.

Another so-called ultrasonic technique has recently been introduced by Baxter-Edwards Healthcare (see *Circulation*, 89(4):1587–92 (1994)). Here the vibrating knife of phako has been replaced with a large ball tip. This device operates by "beating" the ball tip against the material to be removed. Material to be removed is broken up by the physical impact of the tool, or by shock waves and cavitation bubbles created by the vibrating tool.

Specifically with respect to methods for treating occluded arteries, balloon angioplasty is the most commonly used method today for recanalizing obstructed arteries. However, this method remains problematic in situations involving complete obstructions, multisegment and multivessel disease, or late restenosis. R. J. Siegel, M.D., describes a variety of techniques being investigated to resolve these problems, but states: "Each of these technologies also has limitations principally relating to endothelial damage and perforation." (*Circulation*, 78(6):1447 (1988)). In late restenosis, Siegel notes, "[a]ngioplasty carries an additional risk within the first six months. After the procedure is performed, about 35% of the blockages return although that can be relieved by a repeat angioplasty." Id. When blockage re-occurs, secondary surgical intervention is generally necessary immediately.

Ultrasound has also been utilized to remove arterial obstructions. See, for example, Siegel et al., *Lancet, pp. 772–74* (Sep. 30, 1989), Ernst et al., *Am. J. Cardiol.*, 68:242–46 (1991), Siegel et al., *Circulation*, 89(4):1587–92 (1994), DonMicheal et al., U.S. Pat. No. 4,870,953, Guess et al., U.S. Pat. No. 5,069,664, Carter, U.S. Pat. No. 5,269,291, Marcus et al., U.S. Pat. No. 5,295,484, Hashimoto, U.S. Pat. No. 5,307,816, Carter, U.S. Pat. No. 5,362,309, Carter U.S. Pat. No. 5,431,663, and Rosenschein, U.S. Pat. No. 5,524,620. In fact, the highest frequency of acoustical waves disclosed in any of these references as suitable for removing arterial obstructions is 40 MHz (see the Marcus '484 patent), but, the highest frequency that is actually exemplified in Marcus '484 is only 14.4 MHz.

These references teach that ultrasound applied to ablate, or otherwise remove, plaque and thrombus operates by means of mechanical action, heat, or cavitation. Furthermore, these references teach that ultrasonic transducers produce a therapeutic effect at a significant distance from the transducer, 10 cm or more, by focusing the ultrasonic waves.

In addition to ultrasound, numerous groups disclose use of lasers to remove arterial plaque using a diversity of wavelengths (colors of light). Lasers in the infrared and visible wavelengths usually ablate by a thermal mechanism, although some may create shock waves or cavitation bubbles that break down tissue.

The excimer laser is successful in excimer laser keratectomy or "laser sculpting of the cornea" to correct vision. Since this laser operates in the ultraviolet region of the spectrum, it ablates tissue by high energy photons. Certain undesirable side effects that may be encountered in this method include ejection of particles at supersonic velocities, the generation of shock waves, and difficulty in distinguishing healthy from diseased tissue. Also, since the laser operates in the ultraviolet portion of the spectrum, the mutagenic effects of the laser itself and the secondary radiation emitted during the ablation pose possible complications that will not be fully assessed until a long term study is performed.

Another disease state wherein treatment requires destruction of tissue within an inaccessible body cavity is cancer of the prostate. An even greater problem, at least in terms of numbers, is benign prostatic hyperplasia (BPH) for which there are over 400,000 cases per year in the United States alone. For over sixty years, transurethral electroresection of the prostate (TURP) has been the surgical treatment of choice for symptomatic bladder outlet obstruction caused by BPH. For some time, TURP has been considered the "gold standard" for comparison when assessing other treatments for this disease.

Since TURP is not without morbidity or serious complications, the urology community has long sought alternate therapies. Currently, laser prostatectomy is proving to be a far better method for the treatment of BPH. In this method, a light fiber directs the energy of the laser (more often an Nd:YAG laser) into the prostate at a 90° angle with respect to the catheter where the unwanted material is burned. The destroyed tissue initially stays in place and eventually breaks down and is carried away by the urine over a period of six to twelve weeks. During this recovery period, the patient may experience considerable pain and will not regain normal function for some period of time.

Ultrasound treatment of prostate conditions, including prostate cancer and BPH, has been suggested in the art. See, for example, Watkin et al., Brit. J. Urol., 75(supp. 1):1–8 (1995), Gelet et al., Eur. Urol., 29:174–83 (1996), Schaetzle, U.S. Pat. No. 5,443,069, Chapelon et al., U.S. Pat. No. 5,474,071, Granz et al., U.S. Pat. No. 5,526,815, and Oppelt et al., U.S. Pat. No. 5,624,382. The highest frequency of acoustical waves disclosed in these articles is 9.8 MHz in the Watkin article. In the procedures described in this group of references, the ablation of tissue is accomplished through heating or cavitation caused by the ultrasound energy. When the ultrasonic waves are focused, such effects can occur at a significant distance from the transducer, for example, 10 cm or more.

The relatively low ultrasonic frequencies disclosed in the art travel much farther from the transducer through the tissue before being substantially attenuated than is desirable in many applications. In addition, during passage through tissue, the energy of low-frequency ultrasound is converted to heat, physical forces, and acoustical pressures over an undesirably large area, as opposed to confining the energy delivery to the unwanted material or tissue. Furthermore, because of the undesirable time-dependent spread of effects beyond the target area, previous investigators have often used continuous ultrasonic frequency waves in an attempt to ablate the target tissue in as short a time period as possible.

In addition to the use of ultrasound to break down tissues physically, ultrasound has been used to kill tissues by the generation of heat. This use of ultrasound to kill or harm cells at a distance from the transducer is commonly referred to as thermotherapy or hyperthermia. See, for example, ter Haar, Ultrasound in Med. & Biol., 21(9):1089–100 (1995), Pounds, U.S. Pat. No. 4,441,486, Hall et al., U.S. Pat. No. 5,460,595, Unger et al., U.S. Pat. No. 5,558,092, and Chapelon et al., U.S. Pat. No. 5,601,526. Although these references disclose a wide variety of frequencies at which the ultrasound energy is applied to the patient, all of them work by focusing the energy at a point distant from the transducer within the body of the patient. Because the majority of the ultrasound energy impinges upon the focal point, relatively little heating occurs in the tissues between the transducer and the focal point, while the temperature at the focal point may be elevated significantly, causing death to cells and tissues therein.

Ultrasound has also been used to image tissues and non-living structures internally. It is known in the art to use ultrasound at a variety of frequencies, from about 1 MHz to about 600 MHz, for imaging and diagnostic (but not treatment) purposes. See, for example, Harland et al., Brit. J. Dermat., 128:525–32 (1993), Nielsen et al., Ultrasound in Med. & Biol., 19(9):717–25 (1993), Aslanides et al., Brit. J. Ophth., 79:972–76 (1995), Tong et al., Ultrasound in Med. & Biol., 23(6):735–46 (1996), Gniadecka, J. Am. Acad. Derm., 35(1): 37–41 (1996), Chandraratna et al., Am. Heart J., 133:364–68 (1997), Thomas, III et al., U.S. Pat. No. 4,911,170, and Bom et al., U.S. Pat. No. 5,176,141. The purpose of the devices and procedures disclosed in these references is diagnosis. As such, these devices and procedures are not intended to ablate or otherwise remove the target tissues of the patient, but only to provide images thereof. The equipment used in diagnostic imaging operates well at Spatial Peak Temporal Averaged Intensities (I(SPTA)) below or about 100 mW/cm$^2$. In general, significant damage to tissue, such as results in irreversible biologic effects, requires use of I(SPTA) significantly greater than 100 mW/cm$^2$.

U.S. Pat. No. 3,941,122 describes experiments demonstrating the successful liquefaction of lens, cataract, vitreous, and vitreous membrane in excised human, cattle, baboon, and rabbit material using ultra-high frequency ultrasound, but dissolution of other types of tissue or materials is not disclosed therein.

With respect to non-medical uses of ultrasound, vibratory assemblies for cutting material have been used for some time in a wide number of applications. One such apparatus employs a slurry of abrasive particles in conjunction with an ultrasonically vibrating tool, as described, for example, in U.S. Pat. No. 2,580,716. The vibratory energy imparted to the abrasive particles in the slurry hurls them with tremendous acceleration against the surface to be cut, thereby literally chipping away the material. This technique has been applied with great success, particularly in the case of industrial machine tools. Such vibratory assemblies, however, are ineffective for cutting yielding materials and also require a fairly open site so that the interposition of the slurry between the vibrating tool tip and the work surface can be maintained.

In view of the above, it can also be seen that new and better methods and devices are needed for using ultrasonic acoustical waves for surgical procedures. It would be especially advantageous to provide a technique that is tissue specific, highly selective, and very localized for use in such surgical procedures as causing the total disintegration of atherosclerotic build-up, and like materials, without damaging healthy surrounding tissue or producing suspensions of particularized material of such size that they must be artificially transported from the surgical site.

BRIEF DESCRIPTION OF THE INVENTION

In the present invention, methods and devices are provided for utilizing energy from ultra-high frequency acoustical waves to remove unwanted material with specificity from a highly localized site of action, such as a medical treatment site at an inaccessible location within the body.

In one embodiment of the invention, there are provided methods for causing dissolution of unwanted solid or semi-solid material comprising forming ultrasonic acoustical waves having a frequency greater than 50 MHz and a sufficient amplitude to cause dissolution of the unwanted material without substantial damage to surrounding material, and applying the waves to the unwanted material via a zone of acoustical mismatch to cause said dissolution thereto. This effect is enhanced if the generated waves encounter a layer of highly elastic material located at the surface of the unwanted material. Generally, the acoustical waves used in practice of the invention have a Spatial Peak Temporal Averaged Intensity (I(SPTA)) greater than 100 mW/cm$^2$ but provide energy below the cavitation threshold in water at atmospheric pressure.

Such ultra-high frequency sonic energy is highly attenuated over a short distance due to various energy transfer mechanisms at the molecular and macromolecular levels. Therefore, it is preferred to place the ultrasonic transducer in actual contact with the surface of the material whose disruption and dissolution is desired. It is believed that ultra-high frequency energy is absorbed in the immediate region to which it is applied and effectively breaks down tissue because the frequency of such acoustical waves is extremely close to the average resonant frequency of cell structures and macromolecules (whose dimensions are in the same size range (i.e. about 15 µm) as the wavelength associated with the ultra-high frequency ultrasound utilized in the invention methods and devices). Thus, such tissue structures as cells, and components thereof, are put into a vibrational phase resulting in various types of shear and torsional stresses that cause intracellular and/or molecular bonds to break apart, releasing individual cells or clumps of cells, etc. by breaking down cell membranes.

In addition, because the attenuation of ultra high frequency acoustical waves in tissue takes place over a distance less than 1 mm, a radiation pressure is created that aids the dissolution process. An oscillating radiation force that creates alternating compression and rarification causes structures to vibrate longitudinally. This effect is directly proportional to the rate of attenuation of the waves.

To enhance the shear stresses within unwanted material, in the invention methods, the acoustical waves applied to the unwanted soft tissue have a significant transverse wave component in addition to the longitudinal wave component, such as results, in part, from passage of the wave through a boundary between substances of unmatched elastic modulus. For example, it has been discovered that the capacity of ultra-high frequency acoustical waves to dissolve material, such as soft bodily tissue, is enhanced if the acoustical waves are not applied via an "acoustical matching layer." In this situation, there is an impedance mismatch that inhibits propagation of the waves into the unwanted material and contributes to formation of a transverse "shear" component in the propagating wave, thereby enhancing the destructive capacity of the waves as well as the rapid attenuation of the waves within the unwanted material. Mode conversion into a shear wave component can take place even though the medium to be dissolved, such as tissue, will not support a shear stress. In this case, the shear wave is very rapidly attenuated, further localizing the effect of the shear component in accomplishing dissolution of the material.

It has also been discovered that the transverse component of the acoustical wave can be further enhanced if it is applied through an interposing layer of highly elastic material about 1 wavelength in thickness at the operating frequency. Such a layer, in effect, amplifies the waves produced by the transducer. This amplifying effect is greatest if the layer of highly elastic material is fixedly attached to the active face of the transducer.

In the invention methods and devices, ultra-high frequency acoustical waves are delivered to unwanted material in a controllable, localized area, preferably by direct contact with the active face (i.e., working surface) of the ultrasonic transducer, for example, in a repeated rubbing motion (i.e., by erasion). Since this invention, furthermore, does not depend upon the material being battered by acoustical waves or a mechanical structure, it has been discovered that applying ultra-high frequency energy to the unwanted material in pulses, rather than as a continuous wave, may actually reduce the time required to dissolve tissue structures; however continuous wave application is also effective. In pulsed mode operation, for example in pulses of about 10 to about 100 wavelengths in duration, substantially higher wave amplitudes, but lower energy densities, can be applied to the unwanted material with the assurance that any high-frequency vibratory mode imparted to the unwanted material by the acoustical waves will also be absorbed within the localized area of the target tissue. Pulsed mode operation also prevents build-up of heat and reduces the likelihood of cavitation in the target tissue.

For example, at frequencies in the range from 50 to 150 MHz, dissolution only occurs in close proximity to the face of the transducer with the actual distance depending upon the elastic and acoustical properties of the propagating medium (e.g. the unwanted material). Adverse rises in temperature are also prevented, preferably by selecting a pulsed mode of operation (though in some particular instances continuous wave operation and/or cooling may be necessary), such that coagulation of tissue and other disadvantageous side-effects accompanying adverse temperature rises can be avoided.

Whereas relatively low frequency ultrasonic devices break apart unwanted material by mechanical impact or cutting action, the present technique uses a radiated propagating wave of ultra-high frequency ultrasonic energy, preferably in short pulses, to disrupt or dissolve unwanted material into its cellular, subcellular, and/or molecular components in a highly controlled and localized manner.

For many applications, frequencies on the order of 90 to 100 MHz and higher have been shown to be particularly useful in the practice of the invention. The attenuation of ultrasound in soft tissue at such high MHz ranges has been determined to be approximately proportional to the 1.3 power of frequency. Attenuation is also influenced by the acoustical and elastic properties of the unwanted material to which it is applied. For example, acoustical attenuation in tissue is high compared to most materials, about 1 dB/cm/MHz. It follows that if a 100 MHz sound wave is just intense enough to dissolve material at the surface of the transducer, the wave need propagate only a few wavelengths for the effects of attenuation to reduce the intensity of the wave (i.e., to what can be considered a safe level). In tissue, such attenuation occurs within about 0.3 mm and in some materials total attenuation of the acoustical waves occurs within about 1 to 10 wavelengths. This indicates that ultrasound having a frequency in the 100 MHz range can be used to dissolve unwanted material in a very localized region without deleteriously affecting the surrounding material. By contrast, acoustical waves at 1 MHz travel about 3 cm before attenuation reduces its power by one half.

Similarly, wavelength helps to determine the type of destructive forces that operate in target material and the size of the particles generated. When the wavelength of sound is relatively long, cavitation and/or gross mechanical motion produce the break-tip of unwanted material. Such a situation certainly exists if the frequency of the sound is around 40 kHz or below, as in certain prior-art systems before-discussed. When, however, the wavelength of sound is very much smaller, as it is at 100 MHz, the mechanical energy associated with the propagating sound wave breaks down the unwanted material into cellular, macromolecular, and/or molecular components. When used surgically, this process is also described as one of cytolysis because the sound energy disrupts tissue into a subcellular or cellular collection of particles. The depth of material breakdown as measured from the surface of the material to be treated is frequency dependent and the unwanted material can be dissolved to a microscopic level of arbitrarily desired dimensions by selecting the appropriate frequency. These unique features are not possible with prior art techniques that depend on a vibrating mechanical tool, an abrasive slurry, cavitation phenomena, and/or the focusing of acoustical energy, and the like.

It has been discovered that atherosclerotic plaque, thrombus and other buildup, such as fat, can be dissolved by applying 100 MHz transducers to fresh samples according to the invention method. Applicant has employed transducers driven at a resonance frequency by a gated sine wave some 64 microseconds in duration with a pulse repetition rate of one every 400 microseconds. Although absolute power measurements were not made (in fact, it is extremely difficult to make such measurements at these frequencies, especially when operating in a pulse mode), it was determined, using a small thermocouple, that no rise in temperature occurred when the tissue was treated by ultrasound. Examining the ultrasound irradiation process under optical microscopy, no indication of cavitation was noted. Thus, it is concluded that the mechanism causing the tissue to be removed is non-thermal and purely mechanical, with power levels well below the cavitation threshold.

Further, experimentation has led to the theory that the longitudinal wave produced by the transducer undergoes a partial mode conversion at the tissue interface, thereby producing a transverse wave component that shears the tissue at the microscopic level, a thin layer at a time. This effect is aided by a high impedance caused by a large mismatch in elastic properties, such as elastic modulus, between the transducer and the tissue. The longitudinal component of the acoustical waves also plays an important role in disrupting materials by producing the acoustical equivalent of Newton's Rings on the surface of the transducer. Newton's Rings represent rings of high and low pressure regions which radiate outward from a central point across the active face of the transducer. These rings have the effect of producing a further shearing action at the boundary between the transducer and the tissue. Such a process insures that the particle size of the removed tissue is sufficiently small to be easily carried away by the blood or other bodily fluids. Microscopic observation of the products of ultrasonic irradiation by the invention methods and apparatus have confirmed that the particle sizes are no larger than several microns in dimension.

Accordingly, it is contemplated that the invention methods and apparatus can be utilized in a number of surgical and non-surgical applications. For example, the invention methods and apparatus can be utilized for in vivo treatment of atherosclerotic build-up, prostate disorders, cancers, orthopedic and cosmetic surgery, various types of orthopedic surgery, including atheroscopic surgery, and the like. At the microscopic biomedical level, a microscopic transducer operating at about 1 GHz could produce changes at the micron level and would permit "surgery" on cells and cellular structures. At even higher frequencies of about 100 GHz to about 1 THz, "surgery" could be undertaken at the molecular level. For example, chains of DNA could be cut, moved to new locations on the chain, or replaced by alternate sections or sequences. The present invention is also useful in a wide variety of non-surgical applications, including industrial processes wherein the apparatus is used as a cutting tool wherein materials are desired to be selectively destroyed in a very localized region.

In another embodiment of the invention, there are provided novel ultra-high frequency transducers for converting electrical energy to ultrahigh frequency acoustical waves, said transducer comprising a substrate, a piezoelectric element mounted on the substrate and adapted to generate acoustical waves having at least one resonant frequency in the range from about 50 MHz to about 100 GHz, electrodes attached to opposite faces of the piezoelectric element for applying an alternating voltage across the element at the resonant frequency, and a layer of highly elastic material attached to a face of the element. The layer of highly elastic material is generally of uniform thickness and is attached to the active face of the piezoelectric element (i.e., from which sound propagates toward the unwanted material) for the purpose of increasing the amplitude of the acoustical waves generated by application of an alternating voltage across the element, but without a corresponding increase in the maximum value of the voltage applied to the element. Therefore, at a given voltage across the piezoelectric element from the power source, the ultra-high frequency acoustical waves produced by the invention transducer have substantially increased amplitude compared to those produced by such a piezoelectric element in the absence of the highly elastic layer. In a preferred embodiment, the invention transducer is an improvement to the type of transducer known in the art to form a "plane piston source."

Opposite faces of the piezoelectric element(s) have an electrode attached thereto or are otherwise in contact with a power source for applying a voltage across the expansion axis of the element. Electrical leads can be attached to the electrodes, for example by bonding with an electrically conductive solder, to deliver electrical impulses provided by an externally located power source. One or both of the electrodes can be in the form of a thin layer of a metallic substance, such as gold, attached to, or deposited on, the face of the piezoelectric element.

In another embodiment, there is provided apparatus comprising, in combination, an ultra-high frequency energy source adapted to provide energy to an invention transducer, as described above, wherein the transducer is emplaced at the open tip of a casing, wand, or catheter from which the acoustical waves generated by the transducer radiate forward along the axis of the catheter. The catheter is provided with a proximal handle to enable application of the radiating tip to a juxtaposed region of material whose dissolution is desired. For example, at least one lumen of the catheter can be adapted to receive a guidewire channeled through the lumen, which guidewire is connected to the proximal handle or guidewire port. The extension of the guidewire through the distal tip of the catheter is used to manipulate passage of the catheter through the lumen of an artery, or other bodily lumen, as is known in the art. Alternatively, to facilitate passage of the catheter through a curved body lumen, such as the branching of an artery, the substrate is in the shape of a hollow truncated cone with the modified washer-shaped piezoelectric element mounted distally at the end of the cone having the smaller diameter.

Apparatus designed for applying ultrasonic energy used in diagnostic imaging typically applies the ultrasonic energy to the target tissue via an interposed acoustical matching layer (e.g., a layer coating the wand), which layer is selected to maximize propagation of the sonic waves deep into the tissue or other material to be imaged. However, the invention apparatus omits such an acoustical matching layer at the tip of the casing or wand that houses the transducer to assure rapid attenuation of the acoustical waves in the target material, to increase the amplitude of the mechanical wave propagated into the unwanted material, and to enhance production of a shearing force at the interface between the transducer and the unwanted material. Instead of the acoustical matching layer, the invention apparatus comprises an ultra-high frequency transducer having a piezoelectric element with a layer of highly elastic material attached to the active face and mounted at the radiating tip of the casing or wand that houses the transducer. Therefore, when the transducer is placed in contact with the material to be dissolved, as in the currently preferred embodiment, it is the layer of highly elastic material affixed to the element that actually contacts the surface of the unwanted material. Due to the great mismatch in the elastic properties between the unwanted material and the highly elastic layer, mode conversion to a shear wave component is enhanced at the interface with the material to be treated.

An object of the invention, accordingly, is to provide a new and improved process and apparatus for employing ultra-high frequency ultrasound acoustical wave energy at very high amplitude, preferably in short evenly spaced pulses, to dissolve materials, particularly semi-solid and solid materials, such as soft tissue, including atherosclerotic build-up, and the like, to effect highly controllable, selective, and localized ultrasonic tissue disruption, dissolution, and/or erasion without substantial damage to surrounding material.

The novel process and apparatus are particularly adapted to safe removal of atherosclerotic material and other unwanted tissues from the human or animal body at inaccessible locations with the above novel results.

An additional object is to provide a method for selectively disrupting and removing unwanted solid and semi-solid materials of a wide variety of types, such as in industrial and materials science applications, without the use of abrasive substances.

In therapeutic applications, the invention provides the advantage of selectively removing unwanted tissue in a minimally invasive manner without substantial damage to surrounding tissues and structures. This technology has the potential for literally revolutionizing treatment of cardiovascular disease and numerous other fields of surgery and medicine, while significantly reducing the cost as compared to that of conventional procedures.

Other and further objects will be explained hereinafter and are more particularly defined in the appended claims.

DESCRIPTION OF THE INVENTION

Figure 1:
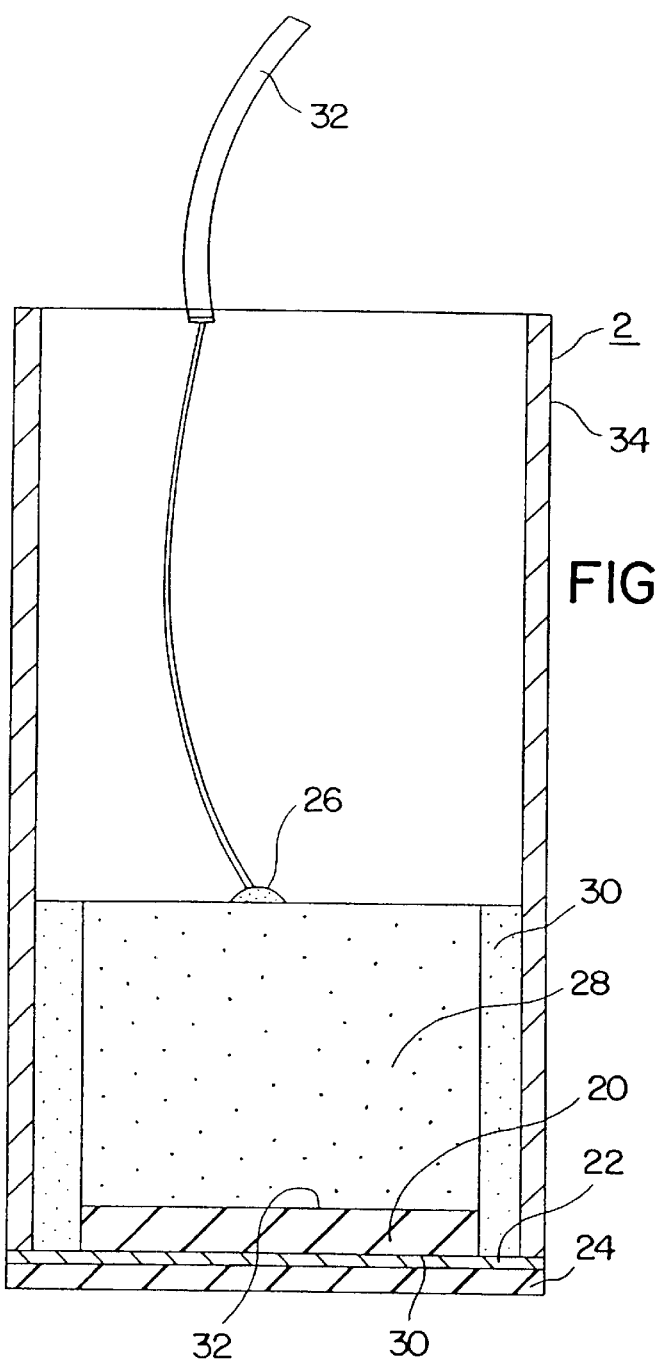
FIG. 1 is a cross-sectional representation of a cylindrical invention transducer.

The overriding principle on which the present invention is based is the fact that the propagation of sound in most materials is highly frequency dependent so that if an ultrasonic pulse is generated that is of sufficient amplitude to be destructive to the medium in which it is propagating, by selecting a sufficiently high frequency, the destructive effects can be localized to a region near the transducer. Thus, if the power is sufficient to destroy the plaque at the transducer assembly, then such destructive effects can be kept localized. The ultra-high frequency acoustical waves are so drastically attenuated as they propagate, any destructive effects can be contained within a very localized region. Through the appropriate selection of ultrasound parameters, such as pulse repetition rate, the destructive effects can be produced without a substantial rise in temperature, e.g., one sufficient to produce a biological effect. The mechanisms for the destructive effects produced by this method are in fact purely mechanical and do not involve other effects, such as cavitation. The application of this technique to plaque should be, in effect, similar to that of an eraser removing a penciled line. That is, in ultrasonic atheroerasion according to the present invention, the ultra-high frequency acoustical waves "erase" the plaque by breaking it down to particles no larger than several microns, e.g., 4–7 microns, such that the resulting material can be easily carried away by the blood.

As used in the present specification and claims, the term "ultra-high frequency acoustical waves" refers to ultrasound having a frequency greater than 50 MHz, for example up to about 100 GHz, or greater. In a currently preferred embodiment, the acoustical waves have a frequency greater than 100 MHz, for example in the range from about 50 MHz to about 150 MHz. In a presently preferred embodiment, the acoustical waves have a frequency of between about 80 MHz and about 120 MHz.

As used in the present specification and claims, the term "ultrasonic erasion" refers to methods of applying ultra-high frequency acoustical waves without an intervening acoustical matching layer to break apart a material at the cellular and/or molecular level, e.g., to create microscopic particles. In particular, in ultrasonic erasion, the surface of the material is repeatedly lightly rubbed or massaged with the radiating locus of the acoustical waves, such as the active face of an ultrasonic transducer which is optionally emplaced at the tip of a catheter. Due to elastic mismatch between the unwanted material and the transducer (e.g., due to the absence of an acoustical matching layer) the acoustical waves propagate into the material through a zone of high elasticity and high impedance mismatch at the interface with the surface of the material to be removed.

The term "erasion" as used herein is synonymous with dissolution, disintegration, and the like, and all of them refer to the method of breaking up unwanted material at the cellular and/or molecular level according to the present invention.

As used in the present specification and claims, the term "ultrasonic atheroerasion" refers to methods of using ultrasonic erasion to remove atherosclerotic build-up. This technique offers the advantage over prior art methods of balloon angioplasty that the atherosclerotic build-up is not merely compressed (with attendant damage to arterial walls), but the build-up is actually removed from the site of blockage. Ultrasonic atheroerasion actually causes dissolution of the build-up into particles so small that such particles can be readily carried away by the bloodstream. Further, it has been discovered that in ultrasonic atheroerasion, when the active face of the invention transducer is in contact with the plaque, the ultra-high frequency waves travel there through no more than about 1 to 10 wavelengths in distance.

As used in the present specification and claims, the term "atherosclerotic build-up" refers to atherosclerotic plaque, thrombus, and fat, as well as calcified plaque and other forms of undesirable build-up that can occur inside the circulatory system, especially in humans.

As used in the present specification and claims, the term "ultrasound surgery" refers to the dissolution of tissues so as to remove or cut tissues as part of a surgical procedure. Thus, "ultrasound surgery" includes ultrasonic atheroerasion within its meaning, as well as a variety of other surgical procedures, when performed using ultrasound energy according to the invention method.

As used in the present specification and claims, the term "applying", when used in reference to applying ultrasound energy to a material, refers to the placement of an ultrasound transducer on or within about 1 to a few wavelengths of the surface of the material, such that the ultrasound energy radiates onto/into/through the material via a zone of acoustical impedance mismatch. When practicing the ultrasound erasion methods of the present invention, because of the rapid attenuation of ultra-high frequency ultrasound in such material as atherosclerotic build-up, and the like, it is typically necessary for the ultrasound transducer to be in actual contact with the material, or within a few wavelengths of the material, in order for dissolution of the material to occur.

As used in the present specification and claims, the term "ultrasound transducer" means any device that is capable of projecting ultrasound energy. Typically, an ultrasound transducer is an electrical device that includes a piezoelectric element, such as a thin crystal, that converts electrical signals into acoustical waves of rapid frequency. However, examples of alternative types of transducers that can be used in practice of the invention methods include magnetostrictive or electrostrictive devices and non-linear laser effects that produce an acoustico-optical effect. Magnetostrictive transducers, oscillate in a direction parallel to an applied magnetic field and are generally driven by applying an alternating or reversing magnetic field parallel to the expansion axis of the element, such as is described in U.S. Pat. No. 5,728,062, which is incorporated herein by reference in its entirety. One or more such transducers can be used simultaneously to accomplish the goals of this invention.

As used in the present specification and claims, the term "hard tissue" refers to hard materials from living organisms. Examples include bone, cartilage, teeth, nails, hair, and the like.

As used in the present specification and claims, the term "soft tissue" refers to soft materials from living organisms. Examples include certain atherosclerotic buildup, prostate tissue, cancer cells, fat cells, and the like.

As used in the present specification and claims, the term "a layer of highly elastic material" means a layer of material having a uniform thickness and an elastic modulus on the order of magnitude of a similar layer of polycrystalline or crystalline diamond, sapphire, boron nitride, alumina, and the like. The minimum thickness of the highly elastic layer is generally limited by such practical considerations as the fragility of such ultra thin layers. Therefore, the thickness of the layer of highly elastic material used to increase the amplitude of the acoustical waves produced by the piezoelectric element is generally in the range from about 1 to 10 times the thickness of the piezoelectric element, with the optimum thickness being about 2 times the thickness of the piezoelectric element or about 1 wavelength of the acoustical waves produced by the piezoelectric element.

In the invention transducer, the term "the active face of the piezoelectric element" means the face of the element from which the acoustical waves propagate. When the piezoelectric element is modified, as in the invention transducer, by attachment thereto of a layer of highly elastic material, the active face includes the highly elastic layer attached to the element.

Accordingly, in the present invention, there are provided methods for causing dissolution of unwanted solid or semi-solid material, said methods comprising: forming ultrasonic acoustical waves having a frequency greater than 50 MHz, and a sufficient amplitude to cause dissolution of the unwanted material without substantial damage to surrounding material, and applying the waves to the unwanted material via a zone of acoustical impedance mismatch to cause said dissolution thereto. It has been discovered that dissolution of semi-solid and solid materials according to the invention method is possible because the ultrasonic waves contain a substantial transverse component (to enhance the shear stresses within unwanted material) in addition to the longitudinal wave component, such as results, in part, from passage of the wave through a boundary between substances of unmatched elastic modulus. The transverse component of the ultrasonic waves is enhanced in the invention methods by omitting use of an "acoustical matching layer" at the interface between the active face of the transducer and the material to be dissolved, as is commonly used in diagnostic procedures. In this situation, there is a high impedance to propagation of the waves into the unwanted material which contributes to formation of a transverse "shear" component in the propagating wave and enhances the destructive capacity of the waves as well as the rapid attenuation of the waves within the unwanted material. Mode conversion into a shear wave component can take place even though the medium to be dissolved, such as tissue, will not support a shear stress. In this case, the shear wave is very rapidly attenuated, further localizing the effect of the shear component in accomplishing dissolution of the material.

It has also been discovered that the transverse component of the acoustical wave can be further enhanced if it is applied through an interposing layer of highly elastic material about 1 wavelength in thickness at the resonant frequency. Such a layer increases the mismatch in elastic properties between the unwanted material and the propagating medium and hence, in effect, amplifies the waves produced by the transducer. This amplifying effect is greatest if the layer of highly elastic material is fixedly attached to the active face of the transducer.

Preferably, the ultrasonic acoustical waves are applied by passing the waves through an interposed layer of highly elastic material located at the surface of the unwanted material. In addition, in presently preferred embodiments, the acoustical waves have a Spatial Peak Temporal Averaged Intensity (I(SPTA)) greater than 100 mW/cm$^2$ and energy levels below those required to cause cavitation in water when used in combination with an ultra-high frequency energy source, such as an electrical generator. Generally, the frequency of the acoustical waves radiating from the transducer is in the range from 50 MHz to about 150 MHz.

Thus, the invention methods provide for removal of zones (e.g., thin layers or patches, and the like, as well as three-dimensional volumes) of unwanted solid or semi-solid material. Such materials include both soft and hard bodily tissues as defined herein, as well as material encountered in industrial environments. The invention methods are particularly suited for ultrasonic erasion of unwanted bodily soft tissues of various types located at relatively inaccessible locations within the body, such as atherosclerotic plaque, benign prostatic hyperplasia, prostate cancer, unwanted fat deposits (as in liposuction), bone and cartilage (as is presently done by conventional cosmetic surgery applications). It is also contemplated that the invention methods and transducers can be used as a general cutting tool, such as an ultrasonic "knife" to cut through material leaving adjacent material unaffected. For example, it is contemplated that a microscopic transducer operating at about 1 GHZ could produce changes at the micron level and would permit "surgery" on cells, while one operating at about 100 GHz to 1 THz could be used to undertake surgery at the molecular level, for example cutting and moving sections of DNA or RNA to a new location in the chain, or splicing new sections or sequences into a chain of DNA or RNA.

In accordance with a particular aspect of the invention, there are provided methods of treating prostatic disease in a subject in need thereof, said method comprising forming ultra-high frequency acoustical waves having a frequency greater than 50 MHz and a sufficient amplitude to cause dissolution of unwanted prostatic tissue without substantial damage to surrounding tissue, and applying the waves to the surface of unwanted prostatic tissue in the subject via a zone of acoustical impedance mismatch to cause dissolution thereof. In one embodiment, the ultrasonic waves are applied to the unwanted prostatic tissue via an interposed layer of highly elastic material, for example, located at the surface of the unwanted prostatic tissue. Types of prostatic disease that can be treated according to this aspect of the invention include benign prostatic hyperplasia, prostate cancer, and the like, or a combination thereof.

In accordance with another aspect of the invention, there are provided methods of treating atherosclerotic conditions in a subject in need thereof, said method comprising forming ultra-high frequency acoustical waves having a frequency greater than 50 MHz and a sufficient amplitude to cause dissolution of the unwanted build-up without substantial damage to surrounding tissue, and applying the waves to the surface of unwanted atherosclerotic tissue in the subject via a zone of acoustical impedance mismatch to cause said dissolution thereto. In one embodiment, the ultrasonic acoustical waves are applied to the unwanted atherosclerotic tissue via an interposed layer of highly elastic material, for example, located at the surface of the unwanted atherosclerotic build-up. Examples of unwanted atherosclerotic buildup suitable for in vivo dissolution using the invention methods include plaque, thrombus, fat, and the like. Ultrasonic atheroerasion, for example, can be performed using the invention method by repeatedly rubbing the surface of the unwanted tissue with the radiating face of one or more ultrasonic transducer(s) which can be at the tip of a casing, such as a catheter.

Although the invention is primarily described for purposes of illustration in connection with its application to surgical procedures, especially the treatment of atherosclerotic build-up and prostate disorders; it is to be distinctly understood that this is by way of illustration only, and that the invention has obviously broader and wider applications, as more particularly delineated in the appended claims.

In another embodiment of the invention, there are provided novel ultra-high frequency transducers for converting electrical energy to ultra-high frequency acoustical waves, said transducer comprising a substrate, a piezoelectric element mounted on the substrate and adapted to generate acoustical waves having at least one resonant frequency in the range from about 50 MHz to about 100 GHz, electrodes attached to opposite faces of the piezoelectric element for applying an alternating voltage across the element at the resonant frequency, and a layer of highly elastic material attached to a face of the element. The purpose of the highly elastic layer is to increase the amplitude of the acoustical waves produced by the transducer at any given frequency, and, as a corollary, to increase the acoustical energy of the waves produced at a given power delivered to the transducer as compared to that produced by a transducer having an unmodified piezoelectric element of otherwise comparable properties.

As illustrated in cross section in FIG. 1, the invention transducer 2 comprises a piezoelectric disc 20 (of 36° rotated Y-cut lithium niobate, 3.17 mm diameter and 0.033 mm thick). Face 30 of the piezoelectric element has an evaporated layer 22 (about 1,000 nm thick) of chromium/gold serving as an electrode. Opposite face 32 of the piezoelectric element is bonded with electrically conductive acrylic cement (not shown) to a pyrolytic graphite substrate 28 (3.17 mm in diameter, and 2.5 mm thick), which substrate is conductive and thus serves as an electrode to face 32 of the piezoelectric element. The substrate and piezoelectric element are encapsulated within an encircling layer 30 of epoxy and held within a hollow cylindrical brass housing 34 (3.7 mm in diameter, 12.7 mm long, 025 mm wall thickness). A layer of highly elastic material 24 (alumina, 0.1 mm thick, bonded with acrylic cement (not shown)) covers the distal end of the transducer, and a dot of silver epoxy 26 attaches an electrical lead 32 to the proximal end of the substrate.

The highly elastic layer interposed between the piezoelectric element and the material to which the acoustical energy is applied in the invention methods and transducers provides a number of desirable characteristics to the ultra-high frequency acoustical waves produced. First, it has been discovered that when the acoustical waves produced by a piezoelectric element are modified by passage through a layer of highly elastic material of appropriate thickness as described herein, the amplitude of the waves is substantially increased. This desirable characteristic enables the dissolution of types of material that cannot be dissolved with otherwise comparable ultra-high frequency piezoelectric transducers.

In many prior art transducers with piezoelectric crystals thin enough to produce ultra-high frequency waves, the crystals tend to break apart at power input high enough to cause dissolution of many materials contemplated by the invention. This failure is attributable to the inescapable fact that production of higher frequencies requires a thinner piezoelectric crystal. Yet power supplied from the power source to the transducer (which is proportional to voltage applied across the crystal) must be increased to provide acoustical waves of sufficient energy (e.g., amplitude) to disrupt the types of tissues and other materials contemplated in the present invention. In the invention transducers, this drawback is overcome by placing a thin layer of highly elastic material, for example having a thickness of about 1 wavelength at the operating frequency, between the piezoelectric element and the material whose dissolution is sought, so that the acoustical waves are transmitted through the layer of highly elastic material. This modification to the piezoelectric transducer increases the amplitude of the ultra-high frequency waves produced by the transducer at any given power input, as compared to those produced by an otherwise identical (i.e., unmodified) transducer.

Second, the layer of highly elastic material increases the mismatch in elastic modulus between the unwanted material (e.g., plaque) and the transducer at the point the acoustical waves enter the unwanted material. As a general rule, the greater the mismatch in elastic modulus, the greater the impedance mismatch. A high impedance interface enhances rapid attenuation of the acoustical waves within the unwanted target material and contributes to formation of a substantial transverse "shear" component of the acoustical waves within the unwanted material whose dissolution is sought. Thus, the highly elastic layer contributes to characteristics of the acoustical waves produced by the invention transducer that enhance the capacity of the waves to cause dissolution of the target material without substantial damage to surrounding tissue.

The transducer may further comprise one or more spacer layer(s) of impedance matching material(s) selected to have an acoustical impedance intermediate between that of the piezoelectric element and the highly elastic layer, which impedance matching layer is interposed between the piezoelectric element and the highly elastic layer. If more than one impedance matching spacer layer is used, it is currently preferred to select material of slightly different impedance for each layer and arrange the layers to create a step gradation in impedance between the piezoelectric element and the highly elastic layer. It is also contemplated that any spacer substance known in the art that transmits the acoustical waves between the piezoelectric element and the highly elastic layer can be interposed therebetween.

Depending upon the Z of the piezoelectric element (as is known in the art), thin films of gold, aluminum, chromium, platinum, copper, and the like, can be used as the spacer substance in the invention transducer. Such materials can also serve as the ground electrode of the transducer and/or can act as a layer of high acoustic impedance for maximum transmission of ultra-high frequency acoustical waves into the highly elastic layer.

The layer of highly elastic material is fixedly attached to the face of the piezoelectric element from which the acoustical waves will propagate. For example, the layer of highly elastic material can be bonded to the piezoelectric element with an epoxy glue or deposited by vapor deposition directly onto the piezoelectric element using thick film deposition techniques. Generally, the layer of highly elastic material covers at least 50% of the surface area of the face of the piezoelectric element. Alternatively, the surface area of the piezoelectric element can be substantially covered by the layer of highly elastic material.

In piezoelectric transducers, the thickness of the piezoelectric element along its expansion axis is generally about ½ the wavelength of the fundamental frequency of the acoustical waves produced by the element. It has been discovered that the greatest increase in amplitude of the acoustical waves produced by modifying a piezoelectric element with a layer of highly elastic material according to the present invention is achieved when the thickness of the highly elastic layer is equal to about one wavelength at the fundamental frequency of the element. However, it is contemplated within the scope of the invention that a highly elastic layer having a thickness of about 1 to about 10 times the thickness of the piezoelectric element along the axis of expansion can be used. However, if the highly elastic layer and/or an impedance matching spacer layer is fixedly attached to the piezoelectric element, the thickness of the vibrating element is increased, causing a corresponding decrease in the frequency of the acoustical waves produced by the transducer.

The material used in the layer of highly elastic material is selected to have high elastic and shear moduli of elasticity. Materials suitable for use as the highly elastic material in the invention transducer include alumina, diamond, boron nitride, sapphire, silicon carbide, silicon nitride, tungsten carbide, titanium di-boride, borazon (boron nitride), aluminum nitride, cermets (composites of metals and ceramics, also known as Ceramic Metal Composites (CMC) and Ceramic Ceramic Composites (CCC), and the like. These highly elastic materials can be high density fully sintered fine grained polycrystalline, or single crystals.

The piezoelectric element can be of any desired shape so long as it is of the required thickness as described above. For example the face of the piezoelectric element can be of any polygonal shape, such as 8 to 16 sided, or any curvilinear shape, such as circular or ovaloid. In a presently preferred embodiment, the piezoelectric element is a washer-shaped flat circular disc having a concentric circular aperture.

The piezoelectric element can be made of any substance known in the art to exhibit the piezoelectric effect of expanding along one axis and contracting along another when subjected to an electric field. Those that are characterized by relatively high frequency constants and very high electromechanical coupling coefficients in the direction of wave propagation are preferred, such as lead zirconate-lead titanate (PZT), lead titanate (LT), lithium niobate 36° rotated for longitudinal waves, and X-cut or 163° rotated Y-cut for shear waves generation (LN), high Qm lead meta-niobate (PMN), lead magnesium niobate (PMgN), lead lanthanum zirconate titanate (PLZT), zinc oxide, aluminum nitride, polyvinyldifluoride (PVDF), and the like. Microstructurally, these materials can be polycrystalline or single crystals.

The substrate upon which the piezoelectric element is mounted in the invention transducer can be of any size or shape suitable to its contemplated utility, as is known in the art. In a presently preferred embodiment, the invention transducer is sized for placement within a casing, such as a catheter, having an opening at the distal tip to expose the active face of the transducer (from which the acoustical waves radiate in a forward direction, along the axis of the casing or catheter). For mounting within the open lumen at the distal tip of a catheter, the invention transducer is about 1 to 5 mm in diameter, and preferably about 2 mm to 4 mm in diameter. In a preferred embodiment, to form a collimated beam of sound (i.e., to act as a plane piston source), the transducer is circular and approximately 10 wavelengths in diameter at the operating frequency. Exemplary materials suitable for use as substrate in the invention transducer include aluminum, magnesium and other light, but electrically conductive materials. Pyrolitic graphite is the substrate presently preferred.

For use in such a catheter, the substrate is generally in the shape of a rod with the modified piezoelectric element mounted at the end of the rod to form a forwardly radiating transducer. The transducer containing the substrate and piezoelectric element can be sized such that a cluster of such transducers are radially distributed within the distal open tip of a catheter. The substrate rod can be hollow to receive a guide wire, and in this embodiment of the invention, the guide wire passes through the hollow rod and extends through the circular aperture at the center of the washer-shaped piezoelectric element.

The substrate can be made of any substance known in the art for use in transducers. However, pyrolytic carbon is presently preferred for use as the substrate in the invention transducer because it conducts electricity and so serves as the back electrode for the piezoelectric element if the piezoelectric element is attached to the substrate via an electrically conducting glue, such as an epoxy glue. In addition, pyrolytic carbon has about the same impedance as lithium niobate, PZT and quartz, which makes it an especially good choice for substrate when any of this group is used as the piezoelectric element.

Figure 2:
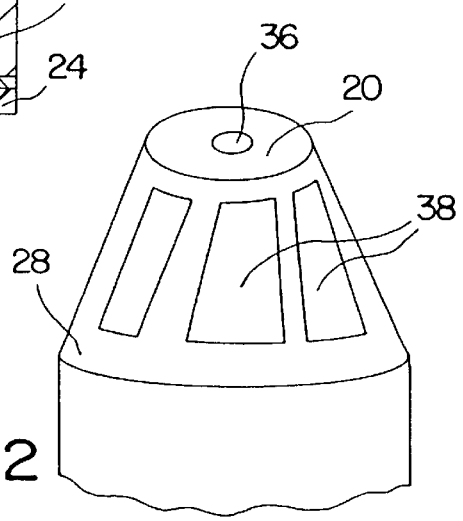
FIG. 2 is a schematic drawing of an invention transducer having a frustro-conical shape and containing a plurality of piezoelectric elements.

In another embodiment, in addition to the above described forward radiating piezoelectric element mounted at the end of the substrate, the invention transducer comprises a plurality of piezoelectric elements, each having a layer of highly elastic material attached as described above and being mounted on the side of the rod like substrate, for example around the periphery of a rod like substrate. These additional piezoelectric elements are also adapted to function as sources of ultra high frequency acoustical waves that radiate in a direction other than that of the forward radiating element, for example, generally normal to the radiation of the forward radiating element. In this embodiment when the invention transducer is mounted into the tip of an elongate sheath, such as a catheter, the active faces of all of the elements are exposed. Consequently, in use within an artery or other confined bodily region, ultrasonic energy will be directed to the sides of the artery to remove unwanted material therefrom, as well as forward along the axis of the artery to remove any blockage to the artery. For example, FIG. 2 shows transducer 2 having a substrate 28 of frustro-conical shape with a washer shaped, forward radiating piezoelectric element 20 having hole 36. Transducer 2 is mounted at the end of the frustro conical shape having the smaller diameter. An array of additional elongate piezoelectric elements 38 are mounted on the sloping surface of the conical substrate. The sloping sides of the transducer having a frustro conical shape may render it more adapted to threading through the arterial tree than the transducer shown in FIG. 1.

Figure 3:
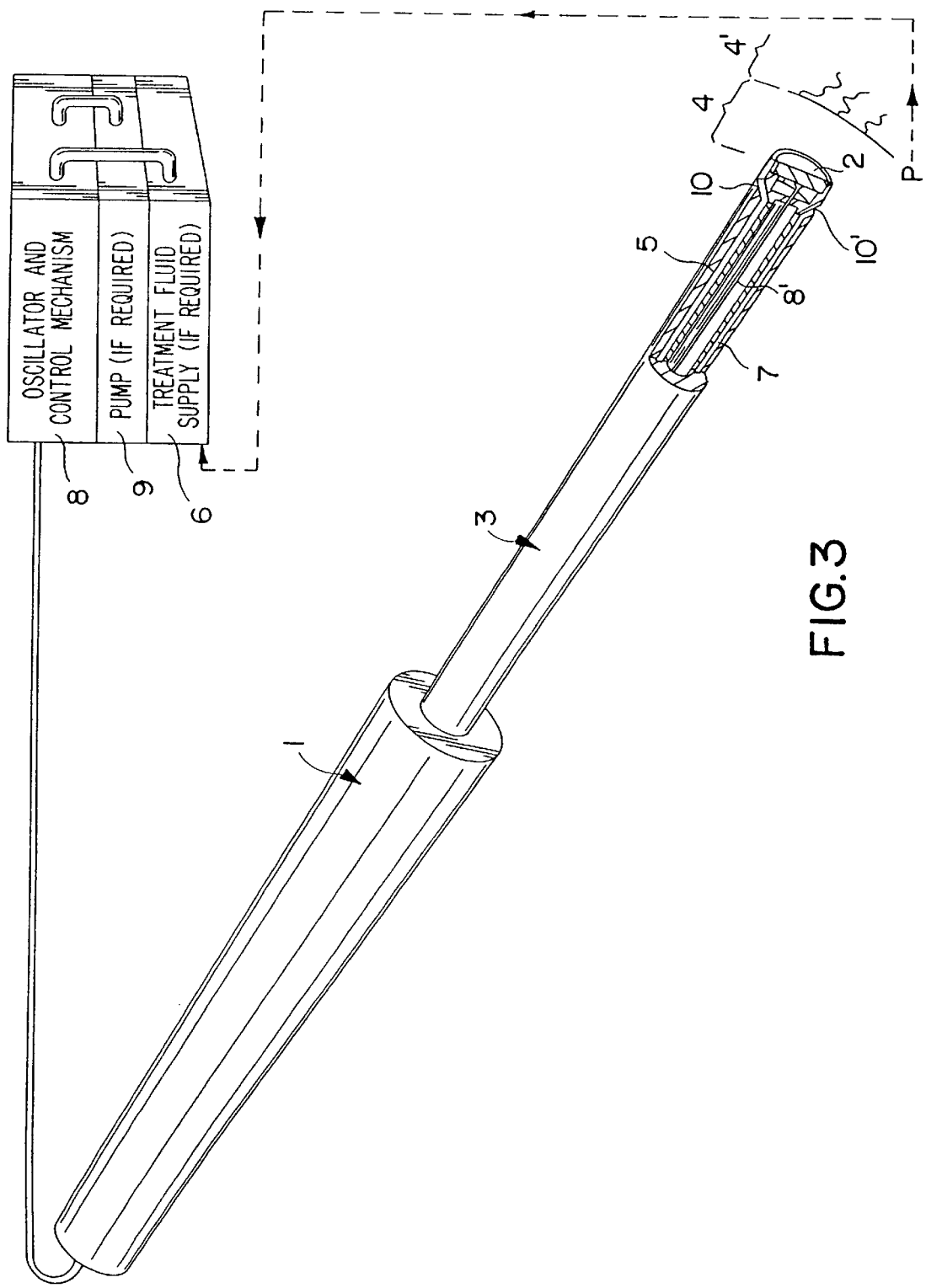
FIG. 3 is a partly schematic and isometric drawing illustrating the invention as applied to a catheter containing the invention transducer at the distal tip.
Figure 4:
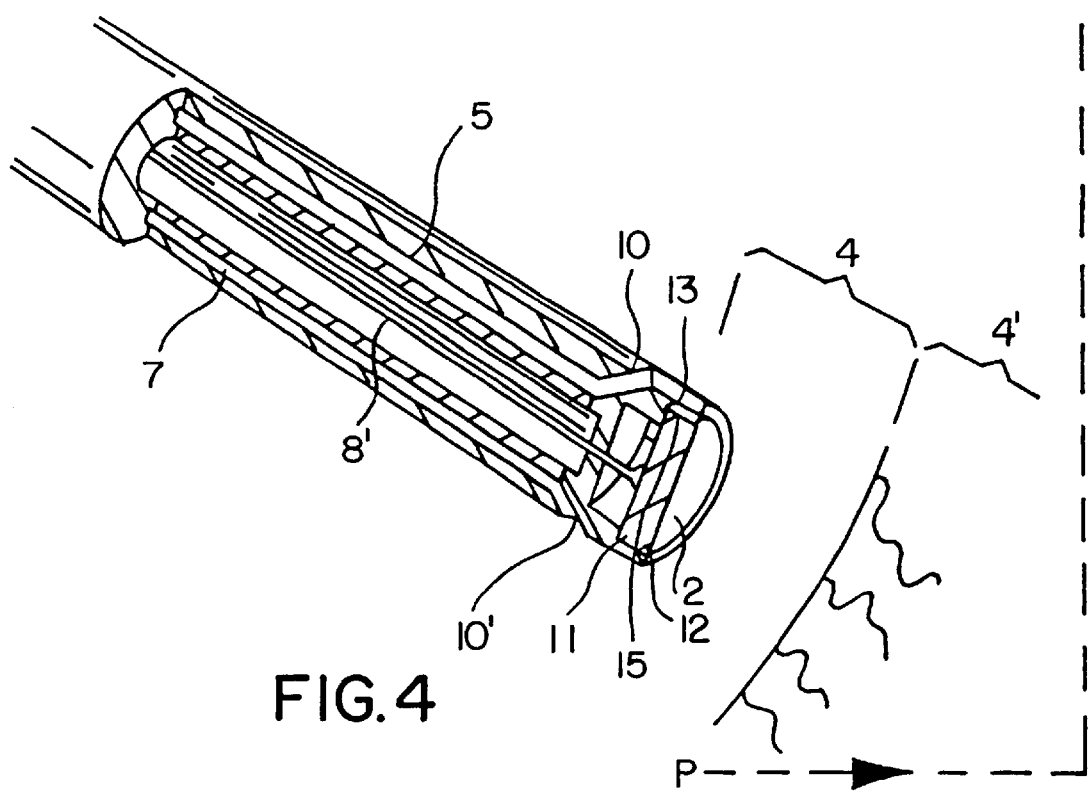
FIG. 4 is a drawing showing an enlargement of the distal tip of the catheter of FIG. 3.

The invention transducers are designed to be contained within a device that is used for their application. For example, FIGS. 3 and 4 illustrate a practical device, incorporating the invention transducer, which utilizes the aforementioned principles of ultra-high frequency ultrasonic energy, this particular instrument lending itself to the performance of delicate surgical procedures in extremely limited and/or inaccessible regions. This device is capable of causing dissolution of both soft and hard tissues with no significant temperature rise and with no damage to peripherally surrounding tissue.

As seen in FIGS. 3 and 4, the device consists of an elongate casing 1 having an open tip 13, within which is mounted a transducer 2. Transducer 2 comprises a piezoelectric disc 11 with a layer of highly elastic material 12 fixedly attached, for example by bonding, to the active face 15 of disc 11. Transducer 2 is mounted on the end of a rod 3, shown here as cylindrical, and serves as a small tip-like source at the P end of a probe, which can be a catheter, for converting electrical energy into ultrasonic energy, piezoelectrically, as is well known in the art. The ultrasonic energy propagates into the unwanted material 4–4' and causes dissolution of the unwanted material as more particularly indicated at 4. Although in many circumstances material will have been dissolved at 4 to a degree such that it need not be physically removed from the surgical site, there are applications wherein the removal of the unwanted material may be desirable. For this latter case, the casing 1 in which the transducer 2 is mounted can be modified, as shown in FIG. 3, to include a lateral longitudinal passage 5 within casing 1 for carrying treatment fluid from a fluid supply 6 through outlet 10, disposed just peripherally rearward of the transducer 2, to the adjacent treatment region where ultrasound is applied; and a similar longitudinal passage 7 for carrying unwanted dissolved material in the treatment fluid away from the first region, under suction. The apparatus also includes an oscillator or generator 8 for supplying electrical energy via conductors 8', shown centrally axially mounted, to the transducer 2, and, where desired, the fluid supply source 6 is used for providing treatment fluid. Suction pump means 9 is provided for withdrawing the fluid, which will contain a suspension of unwanted material, at 10', adjacent the transducer 2. As the radiating tip 13 is applied to the material 4–4', the region adjacent to the operative side can thus be bathed with the treatment fluid. The unwanted material will then naturally run out of the incision, or can be withdrawn under suction at 10'-9.

In operation, pulsed ultra-high frequency electrical signals are applied from oscillator 8 to the transducer 2 so as to produce an ultrasonic impulse wave which propagates from the active face of transducer 2 via layer 12 into the unwanted material 4–4'. The ultrasonic frequency and power level are selected, based on a knowledge of the acoustical properties of the unwanted material, so as to limit dissolving or cytolysis to a specified region; and the pulse length and pulse repetition rate are selected so as to minimize any changes in temperature produced by the ultrasonic wave, as explained more fully herein. For example, in many applications, it will be beneficial to use an ultrasonic oscillator frequency of about 100 MHz, a pulse length adjusted to a range from about 1 $\mu$sec (microsecond) to about 4 $\mu$sec, and a pulse repetition rate adjusted to a range from about 100 to about 500 per second. These parameters will enable the dissolving or cytolysis process to be localized to the region 4 within about 1 mm to about 2 mm from the active face of the transducer, with pulse power on the order of several mW/cm$^2$. The radiating tip 2 may have a cross-sectional dimension on the order of about 10 to 100 times the wavelength selected.

In employing the instrument illustrated, the casing is usually a 1 to 3 lumen catheter with the transducer mounted within one of the lumens in the catheter at the open distal end (i.e., at the tip). For such applications, a transducer having a piezoelectric disc (and highly elastic layer) with a cross-sectional diameter of 2 mm mounted on the end of a thin rod about 4 mm in length has proven effective for causing dissolution of unwanted tissue when mounted within the lumen of a catheter. The surgeon manipulates the casing handpiece 1 to apply the radiating tip 13 extending beyond the handpiece, at treatment sites spaced very short distances from the tip, such as about 1 wavelength to about 1 mm depending upon the elastic and acoustical properties of the propagating materials. Pulses of radiated acoustical wave energy introduce no substantial temperature rise and do not create cavitation effects. Dissolution of unwanted material is confined within a localized area, while the dissolved material 4 is flushed away in the flow of the treating fluid. Beyond 4 at 4', the ultrasonic energy has attenuated to a degree such that no dissolving action takes place. This process continues until all of the unwanted material (e.g., tissue) has been dissolved and, if necessary, removed from the operative site.

When the invention methods and novel transducers are used in medical applications, tissue dissolution, or cytolysis, is highly localized and controllable to prevent damage to tissue or other bodily structures surrounding the treatment site. It may also be desirable to directly aspirate dissolved unwanted material out of the surgical incision or wound hole itself. In such cases, passages in the probe (e.g., catheter) for supplying and withdrawing treatment fluid carry out the dissolved tissue or other bodily matter, may not be needed. For example, adequate irrigation can be supplied through a tube, not shown, affixed to the probe and sized to adequate aspiration from the operative site adjacent to the probe tip. In surgical applications, the invention methods and devices can be used for removal of unwanted material from any body surface or body cavity, natural or surgically created, whether a catheter or a probe is used to apply the acoustical waves to the surgical site.

The invention methods, and devices provide advantages not obtained by use of other treatment modalities currently available or proposed primarily because:

(1) The apparatus used to practice the invention methods is very simple to use. In addition, the apparatus combines a power supply with an ultra-high frequency (and optionally disposable) transducer. It is contemplated that disposable transducers can be economically fabricated using semiconductor or MIMBS technology.

(2) Due to the ultra-high frequency used (generally in the 50 to 120 MHz frequency range), the dissolution of material is extremely localized, minimizing trauma to surrounding materials (e.g., tissues). Also, application of the acoustical waves in short pulses avoids potential thermal effects. Thus, damage to or perforation of the arterial wall is not a concern.

(3) The face of the transducer is preferably placed in contact with the tissue being dissolved, giving the surgeon the touch, tactile feedback, and control which are in keeping with existing surgical training.

(4) Benefits of the reduction in trauma to the tissue being treated include increased precision, reduced postoperative complications, enhanced healing, and shorter hospital stays.

The invention will now be described in greater detail by reference to the following non-limiting examples.

EXAMPLE 1

Attempts at Ultrasonic Atheroerasion Using Prior Art Devices

Tests were conducted over a two year period to attempt to apply ultrasound technology to removal of atherosclerotic plaque and thrombus. Commercially available transducers and transducer components, such as the transducer described in U.S. Pat. No. 3,941,122, which employs an acoustical matching layer between the transducer and the target material, were used to test the ability of the system to remove various types of soft tissue from biological tissue samples. First, the tests described in the '122 patent were repeated with success, using samples of fresh lens and other ophthalmic tissue provided by several local ophthalmologists. This same experimental system was then successfully applied to a number of thrombus samples. However, numerous attempts to dissolve atherosclerotic plaque in fresh in vitro samples were not successful due to failure of the experimental systems to produce sufficient acoustical amplitude from the transducers.

Many similar attempts were made to obtain appropriate transducers, both commercially as well as by fabrication, without success. It was concluded that transducer technology was not developed to the point that ultra-high frequency transducers of sufficient power could be constructed, and that the application of ultra-high frequency acoustical waves to removal of atherosclerotic plaque and tissues of comparable hardness was not feasible using transducers and/or techniques available at that time.

EXAMPLE 2

Ultrasonic Atheroerasion

To determine the effect of having an acoustical matching layer between the material to be treated and the active face of the transducer, comparative tests were conducted using an ultra-high frequency ultrasound device capable of generating an output of 90 MHz pulsed ultrasound was applied to atherosclerotic build-up in excised human material. For performing the experiments detailed in these examples, a number of small transducers, ranging from 50 to 120 MHz in frequency, were produced. Each transducer, designed to operate as a plane piston source, was a flat disc with a diameter of about 2 mm mounted on the end of a stainless steel cylinder 2 cm in length. A generator was used to drive a resonant frequency lithium niobate crystal at its fundamental frequency. The pulse length was about 10 $\mu$sec and with a pulse repetition rate of about 1000 per second. The biological sample was held with forceps and subjected to the active face of the transducer or the face of the transducer was covered with a layer of polyethylene rubber as an acoustical matching layer. The power was slowly increased until dissolving or cytolysis was observed at the face of the transducer. In all tests wherein the matching layer was omitted, dissolving or cytolysis was successful and appeared to be localized to a region normal or perpendicular to and well within 1 mm of the face of the transducer; whereas in the studies in which an acoustical matching layer was employed, cytolysis of the plaque could not be achieved.

A small thermocouple was placed at various positions within some of the samples tested. Only small variations in temperature were recorded during erasion. At a distance of about 2 mm from the transducer surface, the maximum rise in temperature was less than 1° C.

Further in vitro studies were conducted with the matching layer omitted on numerous samples of thrombus in various stages of development as well as plaque of assorted types. All of the samples of thrombus were easily dissolved. Similar results were obtained with both fatty and fibrotic plaque, although the time and acoustical power required were somewhat greater than for thrombus. A typical mixed plaque, 1 $cm^3$ in size, could be dissolved by rubbing the transducer over the plaque for 2 to 3 minutes. This process of erasion seems similar to that of an eraser removing a penciled line. Heavily calcified plaque was also dissolved, but only with the use of higher acoustical power for longer intervals of time.

During the course of the experiments described herein, an important observation was made concerning the selectivity of the process. The plaque was being dissolved with no adverse effect to the arterial wall. Even lengthy application of the transducer directly to the normal arterial wall, or to a position on the wall where plaque had been removed, produced no noticeable effect. Thus, through the appropriate selection of ultrasound parameters, plaque and thrombus can be selectively dissolved without harming the wall of the artery. This feature is not provided by other known methods for treatment of cardiovascular disease and offers a significant advantage over such methods.

EXAMPLE 3

Improved Ultrasound Transducers

To obtain even better results, several transducers were fabricated with 2 mm diameter active elements in the form of a disc mounted on the side of a steel rod, also 2 mm in diameter. The rod itself was several centimeters in length to afford ease of handling. The transducers had center frequencies between 80 and 100 MHz and were capable of producing acoustical intensities double that of the devices used when performing the experiments described in Example 2 (using the same electronics and ultrasound parameters) in spite of their much smaller size. These transducers were applied without an intervening acoustical matching layer to the aorta of rabbits genetically bred to acquire atherosclerotic plaque. The plaque was easily dissolved or erased when treated with ultrasound according to this method.

EXAMPLE 4

Ablation of Dead Tissue Left Behind by Conventional Prostate Treatment Methods

Prostate tissue burned by a laser obtained from a local urologist representing BPH and prostate cancer has been examined using equipment utilizing the procedure and invention transducer described in Example 3. Tissue characteristic of BPH was readily dissolved using an intermediate power level, although the vascular bed in the tissue remained intact. It is believed that the tissue of the vascular bed could also be removed by delivering a higher power level to the transducer.

The success of this experiment presents the opportunity for a change in the manner in which laser prostatectomy is done. Following the laser application, an ultrasound catheter would be inserted to dissolve and wash out the burned tissue. The ultrasound would also treat the prostate wall, and is expected to result in less pain and sensitivity. The whole procedure would be only slightly longer in time than the laser treatment alone, and would have the major advantage that the patient would experience full recovery in a substantially reduced period of time-no painful six to twelve week waiting period.

Additionally, it is expected that the method of the present invention would also work with other methods currently used to "burn" the excess prostate tissue, including microwave and high-power (but much lower frequency) ultrasound.

EXAMPLE 5

Ablation of Prostate Tissue

Additionally, the ultrasound method of the present invention can be used to dissolve prostate tissue directly, without using a laser or some other form of energy. Examination and experimentation on tissue samples indicates that the ultrasound method of the present invention can indeed be used to remove unwanted prostate tissue, largely because as the BPH process develops, the tissue becomes more fibrotic giving it different elastic and acoustical properties than the surrounding healthy tissue. Thus, the present method allows BPH to be treated in essentially a one-step process, with ultra-high frequency ultrasound doing the work of the laser (or other energy sources) as well as the subsequent dissolution of the unwanted material. The combination of ultrasound parameters required to dissolve BPH leaves the vascular bed intact to provide a framework for regrowth of healthy tissue. Application of the same transducer but with different ultrasound parameters (e.g., higher power levels) removed the remaining capillaries.

Further studies were conducted using several tissue specimens representing benign prostatic hyperplasia (BPH) and prostate cancer. Using the same equipment and ultrasound parameters described in Example 2, it was possible to dissolve tissue associated with BPH, although the vascular bed remained intact. By going to higher power levels, the vascular bed could also be removed. For the tissue specimens containing samples of prostate cancer tissue, intermediate power levels proved sufficient to dissolve the prostate cancer tissue.

EXAMPLE 6

Ablation of Cancer

The selectivity of the method when applied to samples associated with BPH indicates that the present invention will work for the treatment of even advanced liver cancer. Here, the diseased tissue could be removed leaving the vascular bed intact and thereby providing a structure and form for tissue regeneration.

Using the ultrasound method of the present invention to remove tissue without removing the vascular bed also has significant advantages. For example, it is expected to be possible to remove a tumor without removing adjacent normal tissue. With the vascular bed intact, in many cases, normal tissue will then grow to replace the tumor. This observation in itself could have significant applications in a wide range of medical specialties.

Although cancer of the prostate develops by a process that is not fully understood, it appears that a hard nodule develops after what is probably many years of growth and development. An examination of tissue samples clearly indicates that the ultrasound method of the present invention could indeed dissolve the tumor while leaving the normal tissue intact.

EXAMPLE 7

A series of plane piston source transducers were fabricated to be 2 mm in diameter, mounted in a one inch long steel tube, and ranging in frequency between about 50 and 120 MHz. A short coax cable ran from the transducer housing to a standard microdot connector. No attempts were made to match the electrical impedance of the transducer (2 to 5 Ohms) with that of the RF electrical source (50 Ohms). This impedance mismatch significantly reduces the efficiency of the device, but still provides a tool with which to explore the ultrasound parameter space for ultrasonic erasion.

The plane piston source transducers were fabricated to be of three configurations: (1) without an acoustical matching layer over the active face, (2) having an acoustical matching layer (polyethylene rubber matched to tissue), and (3) having a layer of highly elastic material (polycrystalline alumina) mounted directly on the active face of the transducer. Applications of the three configurations of transducer to fresh bone marrow (simulating plaque in a vein graft) showed that configuration (3) (lacking an acoustical matching layer and having a layer of highly elastic material mounted on the active face) worked best. A 2 mm by 1 inch column of bone marrow was liquefied in 1 minute at very low duty factors (a 64 microsecond pulse repeated every 400 microseconds and with less than 100 volts across the transducer) using configuration (3). On the other hand, configuration (2) having an acoustical matching layer had no effect and configuration (1) had an effect, but was not as effective at causing dissolution of the bone marrow as configuration (3).

While the invention has been described in detail with reference to certain preferred embodiments thereof, it will be understood that modifications and variations are within the spirit and scope of that which is described and claimed.

That which is claimed is:

1. A method of tissue dissolution comprising:
   providing a device comprised of at least one acoustical transducer and least one highly elastic layer having an outer boundary and providing an impedance mismatch interposed between the at least one acoustical transducer and a local region of the tissue;
   placing the device so that the at least one highly elastic layer of the at least one transducer is in contact with a surface of the local region of the tissue;
   generating by the at least one acoustical transducer, a plurality of acoustical waves comprising at least one series, wherein each acoustical wave is within an ultra-high frequency range; and
   applying the at least one series of the generated plurality of acoustical waves, wherein each acoustical wave possesses sufficient amplitude for the at least one series to dissolve the local region of the tissue via the at least one highly elastic layer;

whereby the local region of the tissue is dissolved.

2. The method of tissue dissolution of claim 1 wherein the at least one highly elastic layer is substantially one acoustical wavelength in thickness.

3. The method of tissue dissolution of claim 1 wherein the frequency range of the plurality of acoustical waves is between about 50 megahertz and about 150 megahertz.

4. The method of tissue dissolution of claim 1 further comprising the step of rubbing the at least one highly elastic layer of the device across the surface of the local region of the tissue.

5. The method of tissue dissolution of claim 1, wherein the providing of the device further comprises placing the device within a catheter prior to applying the acoustical waves.

6. The method of tissue dissolution of claim 1, wherein the generated acoustical waves comprise a substantial transverse component.

7. The method of tissue dissolution of claim 1, wherein the generated acoustical waves comprise a substantial transverse component and a longitudinal component.

8. The method of tissue dissolution of claim 1, wherein the generated acoustical waves comprise shear waves propagating from the outer boundary of the at least one highly elastic layer.

9. The method of tissue dissolution of claim 1, wherein the plurality of applied acoustical waves comprise a plurality of acoustical waves of constrained amplitudes wherein each of the plurality of acoustical waves has acoustical energy and wherein the acoustical energy of each wave comprising the plurality of acoustical waves of constrained amplitudes is below a cavitation threshold in water.

10. The method of tissue dissolution of claim 1 wherein the frequency of the plurality of acoustical waves is at least 50 megahertz.

11. The method of tissue dissolution of claim 1 wherein the frequency range of the plurality of acoustical waves is between 50 megahertz and 120 megahertz.

12. The method of tissue dissolution of claim 1 wherein the frequency range of the plurality of acoustical waves is between 50 megahertz and 150 megahertz.

13. The method of tissue dissolution of claim 1 wherein the frequency range of the plurality of acoustical waves is between 50 megahertz and 200 megahertz.

14. The method of tissue dissolution of claim 1 wherein the frequency range of the plurality of acoustical waves is between 200 megahertz and 1 gigahertz.

15. The method of tissue dissolution of claim 1 wherein the frequency range of the plurality of acoustical waves is between 1 gigahertz and 100 gigahertz.

16. The method of tissue dissolution of claim 1 wherein the frequency range of the plurality of acoustical waves is between about 100 gigahertz and about 1 terahertz.

17. A method of tissue dissolution comprising:

providing a device comprised of at least one acoustical transducer and least one highly elastic layer having an outer boundary and providing an impedance mismatch interposed between the at least one acoustical transducer and a local region of the tissue;

placing the device so that the at least one highly elastic layer of the at least one transducer is in contact with a surface of the local region of the tissue;

generating by the at least one acoustical transducer, a plurality of acoustical waves comprising at least one series, wherein each acoustical wave is within an ultra-high frequency range; and applying the at least one series of the generated plurality of acoustical waves, wherein each acoustical wave possesses sufficient amplitude for the at least one series to dissolve the local region of the tissue via the at least one highly elastic layer;

wherein the at least one series of the generated plurality of acoustical waves are in durations of ten to 100 cycles divided by the frequency;

whereby the local region of the tissue is dissolved.

* * * * *